(12) United States Patent
Song

(10) Patent No.: US 12,419,734 B2
(45) Date of Patent: Sep. 23, 2025

(54) SURGICAL THREAD

(71) Applicant: HYUNDAE MEDITECH Co., Ltd., Wonju-si (KR)

(72) Inventor: Mi Hee Song, Wonju-si (KR)

(73) Assignee: HYUNDAE MEDITECH CO., LTD., Wonju-si (KR)

( * ) Notice: Subject to any disclaimer, the term of this patent is extended or adjusted under 35 U.S.C. 154(b) by 144 days.

(21) Appl. No.: 18/531,032

(22) Filed: Dec. 6, 2023

(65) Prior Publication Data

US 2024/0358487 A1 Oct. 31, 2024

(30) Foreign Application Priority Data

Apr. 27, 2023 (KR) ........................ 10-2023-0055487

(51) Int. Cl.
*A61F 2/00* (2006.01)

(52) U.S. Cl.
CPC .......... *A61F 2/0063* (2013.01); *A61F 2/0059* (2013.01); *A61F 2240/00* (2013.01); *A61F 2250/0037* (2013.01); *A61F 2250/0039* (2013.01)

(58) Field of Classification Search
CPC .. A61F 2/0063; A61F 2/0059; A61F 2240/00; A61F 2250/0037; A61F 2250/0039; A61F 2002/0068; A61F 2220/0016; A61B 2017/00964; A61B 2017/00792; A61B 2017/26176; A61B 2017/00747; A61B 2017/06185; A61B 2017/0619; A61B 17/06166
See application file for complete search history.

(56) References Cited

FOREIGN PATENT DOCUMENTS

| KR | 20-0344226 Y1 | 3/2004 |
|----|---|---|
| KR | 101182337 B1 | 9/2012 |
| KR | 10-1337465 B1 | 12/2013 |
| KR | 101534821 B1 | 7/2015 |
| KR | 20160066831 A | 6/2016 |
| KR | 10-1635580 B1 | 7/2016 |
| KR | 101825736 B1 | 2/2018 |
| KR | 102057894 B1 | 12/2019 |
| KR | 10-2022-0106907 A | 8/2022 |

*Primary Examiner* — Ryan J. Severson
(74) *Attorney, Agent, or Firm* — Rabin & Berdo, P.C.

(57) ABSTRACT

The present disclosure provides a surgical thread including a cog thread and a mesh thread surrounding the cog thread and assembled therewith, wherein, in the mesh thread, first and second regions with different mesh shapes are repeatedly disposed in a longitudinal direction of the cog thread.

11 Claims, 5 Drawing Sheets

SURGICAL THREAD

CROSS-REFERENCE TO RELATED APPLICATION

This application claims priority to and the benefit of Korean Patent Application No. 2023-0055487, filed on Apr. 27, 2023, the disclosure of which is incorporated herein by reference in its entirety.

BACKGROUND

1. Field of the Invention

The present disclosure relates to a surgical thread, and more particularly, to a surgical thread devised to, when a surgical thread having a form in which a thread having cogs formed on a surface thereof (hereinafter referred to as "cog thread") is positioned at the center of a thread made of tubular mesh (hereinafter referred to as "mesh thread"), among surgical threads used in lifting treatment to improve wrinkles or sagging of the skin, is inserted subcutaneously, suppress the mesh thread from being pushed in a direction opposite to a direction of insertion.

2. Discussion of Related Art

Lifting treatment in which a surgical thread is inserted subcutaneously to induce collagen production or pull tissue is performed to improve wrinkles or sagging of the skin.

Surgical threads inserted subcutaneously for lifting treatment are classified into mono threads having a smooth surface and cog threads having cogs formed on a surface thereof. A mono thread does not have a lifting function but is used for the purpose of inducing collagen formation therearound to improve skin elasticity, and the cog thread disclosed in Korean Utility Model Registration No. 20-0344226 is used for the purpose of being inserted subcutaneously to pull subcutaneous tissue and the skin with the cogs.

Meanwhile, a mesh assembly in the form of a mesh as disclosed in Korean Patent Registration No. 10-1337465 is also used in lifting treatment. In recent years, mesh threads in which a mesh member has a tubular shape have been available on the market. The growth of living tissue is induced through openings of the mesh thread to obtain a skin pulling effect.

When the mesh thread is used, a pulling force is weaker compared to the cog thread before the growth of living tissue is induced, and the cog thread has a problem in that, since a surface of the mono thread is partially cut out to form cogs, a tensile strength is weakened. In order to address such problems, as in Korean Patent Registration No. 10-1635580 and Korean Patent Publication No. 10-2022-0106907, a surgical thread having a form in which a cog thread is inserted into a tubular mesh thread, and protrusions of the cog thread protrude to the outside of the mesh thread through openings of the mesh thread has been developed.

Since the surgical thread having the form in which the cog thread is positioned inside the tubular mesh thread (hereinafter referred to as "surgical thread") has a problem in that the thread forming the mesh is loosened at an end thereof, adhering one end of the mesh thread to the cog thread by thermocompression bonding to prevent loosening of the mesh has been disclosed in Korean Patent Registration No. 10-1635580. Adhering a cog thread (10) and a mesh thread (20) at one side end ("A" in FIG. 1) of a surgical thread (1) as in FIG. 1 using a method such as heat fusion or application of an adhesive is disclosed in Korean Patent Publication No. 10-2022-0106907. The adhesion is performed at the end in this way to either facilitate fitting of the surgical thread into a needle (21) of a cannula (20) used to insert the surgical thread subcutaneously or prevent loosening of the mesh at the end of the surgical thread. When the adhesion is performed at only one side as in Korean Patent Publication No. 10-2022-0106907, there is still a problem in that loosening of the mesh occurs at the other end ("B" in FIG. 1) of the surgical thread where the mesh thread is not adhered to the cog thread.

In order to prevent this problem, the end (B) positioned outside the needle (21) of the cannula (20) and where the mesh thread is not adhered to the cog thread, among the ends of the surgical thread, is fixed to the needle (20) of the cannula (20) using a ring (22) or the like in some cases (see FIG. 2).

The end fixed to the ring (22) or where the mesh thread is adhered to the cog thread as described above has a problem in that, when the surgical thread enters the skin, as in FIG. 2, the mesh thread is pushed toward the end (toward a side opposite to a direction of insertion of the cannula), and a portion (C) near the end is inflated.

Korean Patent Registration No. 10-1635580 attempts to address this problem with a form in which mesh threads each having a predetermined length are disposed at predetermined intervals in a longitudinal direction of a cog thread and both ends of each mesh thread are adhered to the cog thread. However, there are problems in that the manufacturing process is complicated, and the number of sites of adhering portions where degeneration occurs due to heat fusion or an adhesive is used increases.

RELATED ART DOCUMENTS

Patent Documents

KR 20-0344226 Y1, Mar. 11, 2004, FIG. 2
KR 10-1337465 B1, Dec. 6, 2013, FIG. 2A
KR 10-1635580 B1, Jul. 20, 2016, claim 2
KR 10-2022-0106907 A, Aug. 1, 2022, FIG. 1

SUMMARY OF THE INVENTION

The present disclosure is directed to providing a surgical thread that prevents a mesh thread from being pushed toward an end of the surgical thread, is easy to produce, and eliminates or minimizes heat fusion or the application of an adhesive.

The present disclosure provides a surgical thread including a cog thread and a mesh thread surrounding the cog thread and assembled therewith, wherein, in the mesh thread, first and second regions with different mesh shapes are repeatedly disposed in a longitudinal direction of the cog thread.

A size of an opening of the first region may be larger than a size of an opening of the second region.

A diameter of the first region may be larger than a diameter of the second region.

An inner side surface of the mesh thread of the second region may be in full contact with the cog thread.

The cog thread at a position corresponding to the second region may have a plurality of cogs formed thereon toward different ends of the surgical thread.

A length of the first region may be longer than a length of the second region.

The length of the second region may be in a range of 3 mm to 10 mm.

Both ends of the surgical thread may be formed as the second region.

The cog thread and the mesh thread may be adhered by an adhesive or heat fusion at the both ends of the surgical thread.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, the present disclosure will be described in more detail according to embodiments thereof with reference to the accompanying drawings.

A surgical thread of the present disclosure may be made of a biodegradable polymer material such as a copolymer of polylactic acid, a copolymer of polydioxanone, a copolymer of lactic acid, and a copolymer of glycolic acid.

Cogs of a cog thread may be formed by thermoforming or by obliquely cutting out a surface of the thread.

The surgical thread of the present disclosure may be manufactured by supplying the cog thread to the center of a mesh thread when the mesh thread is being formed by a loom, a braiding machine, or a rotary spinning machine.

Alternatively, the surgical thread of the present disclosure may be manufactured by inserting the cog thread into the mesh thread produced by a loom, a braiding machine, or a rotary spinning machine.

Figure 1:
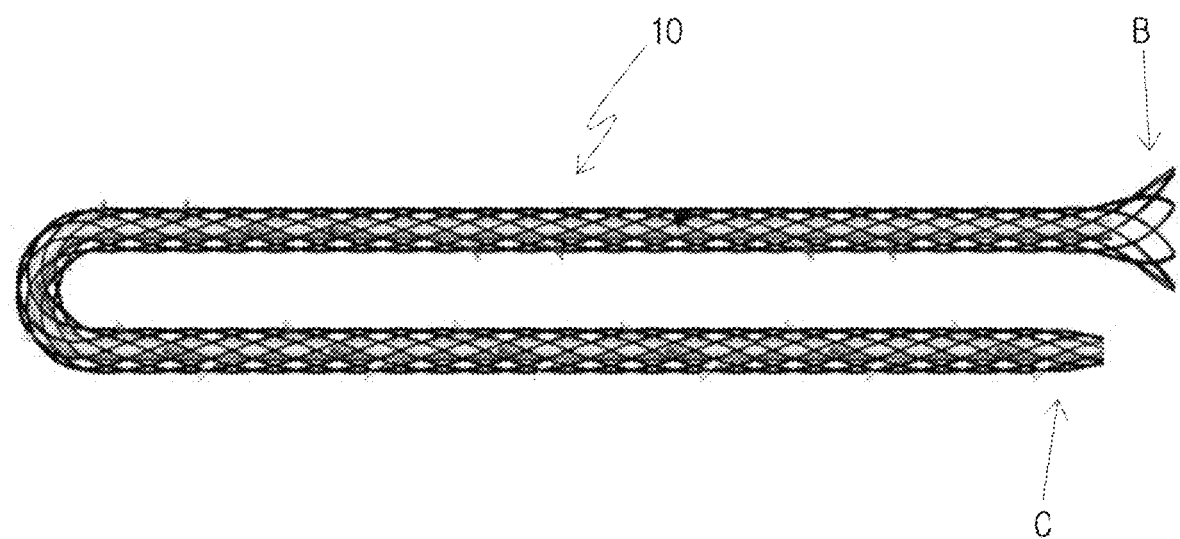
FIG. 1 is a view illustrating the form of a conventional surgical thread.
Figure 2:
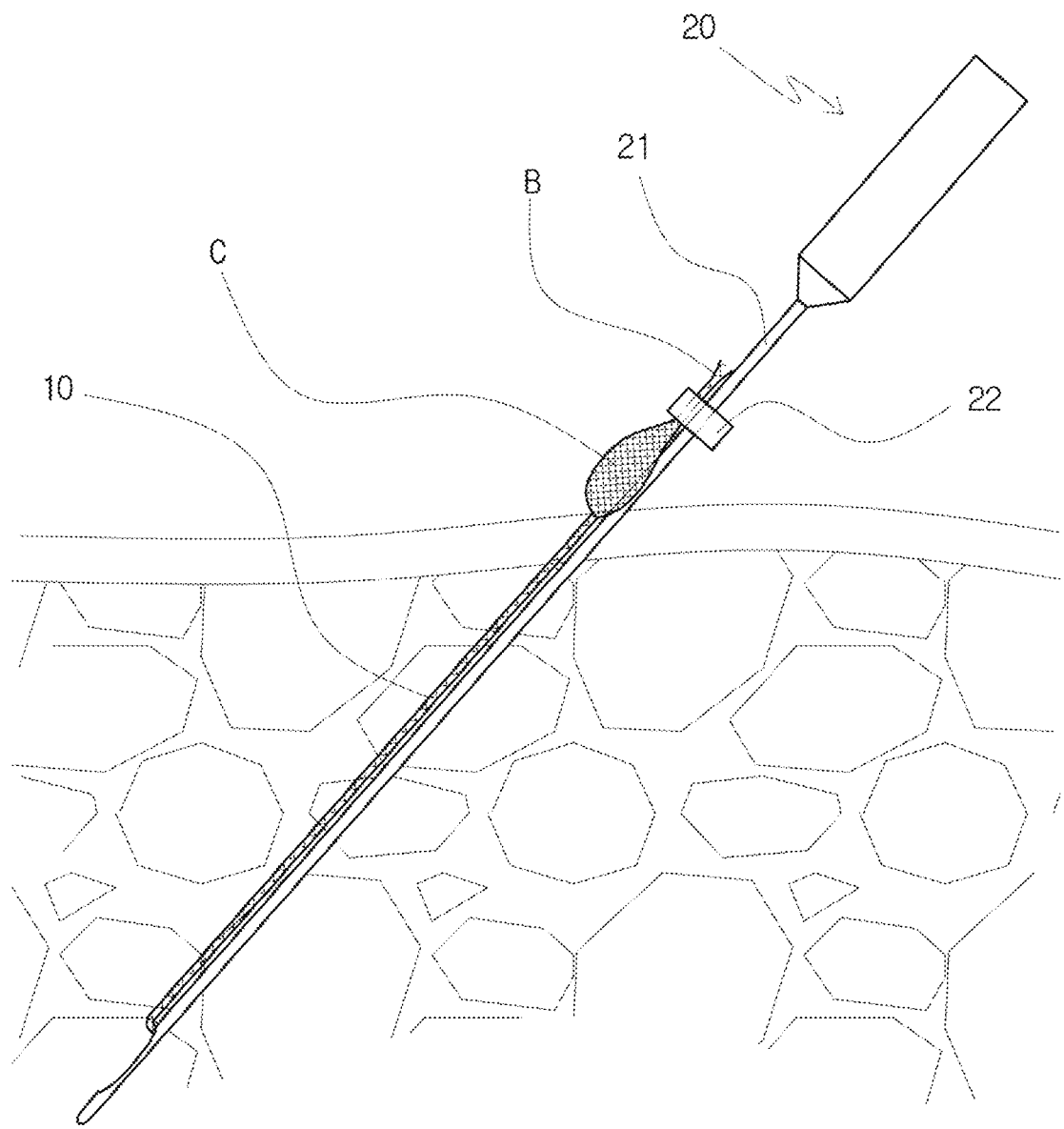
FIG. 2 is a view illustrating the form of treatment using the conventional surgical thread.
Figure 3:
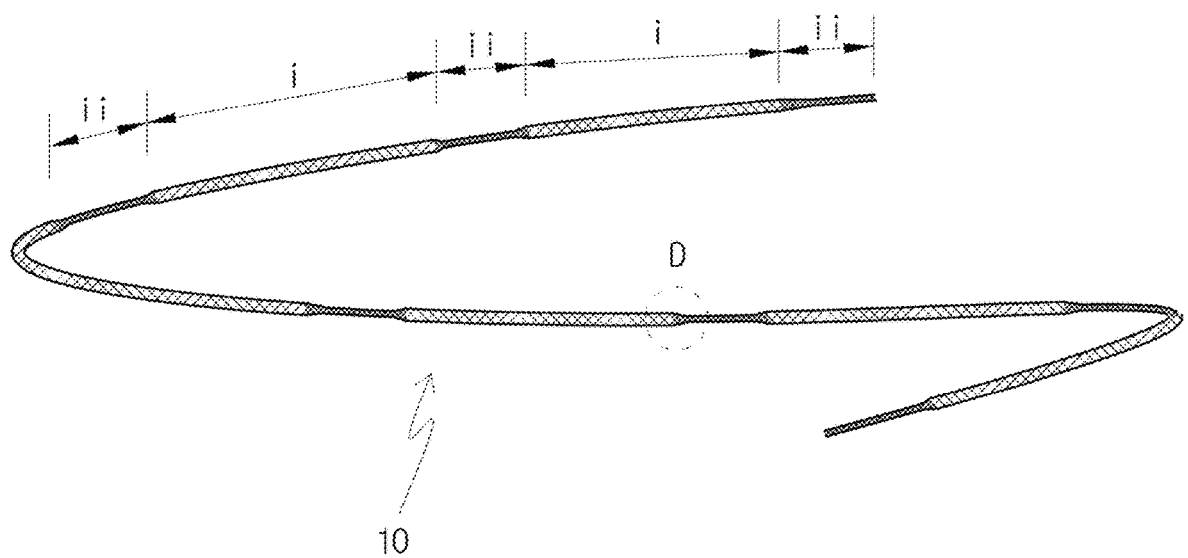
FIG. 3 is a view illustrating the form of a surgical thread according to one embodiment of the present disclosure.
Figure 4:
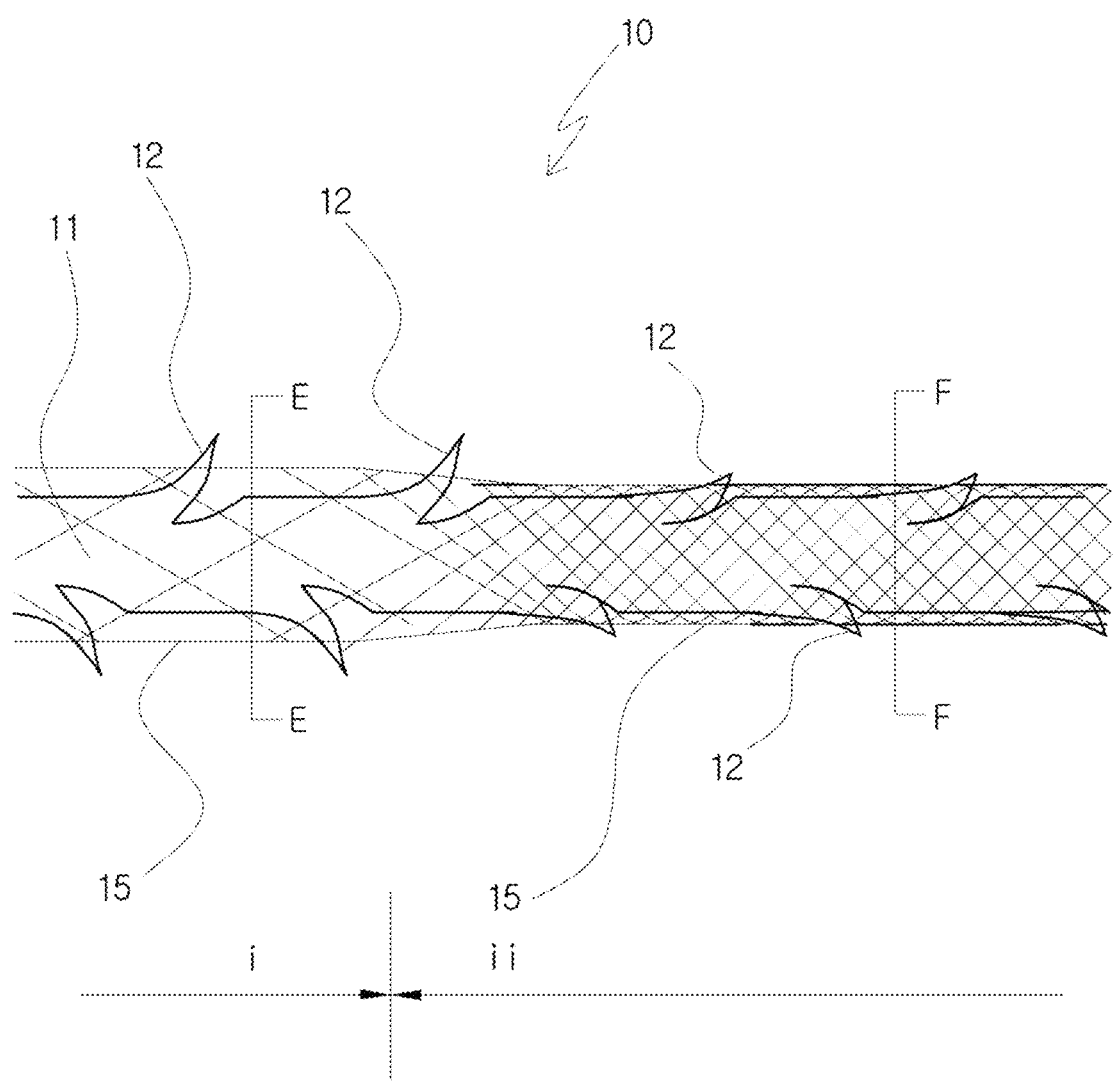
FIG. 4 is a partially enlarged view of first and second regions of the surgical thread according to one embodiment of the present disclosure.
Figure 5:
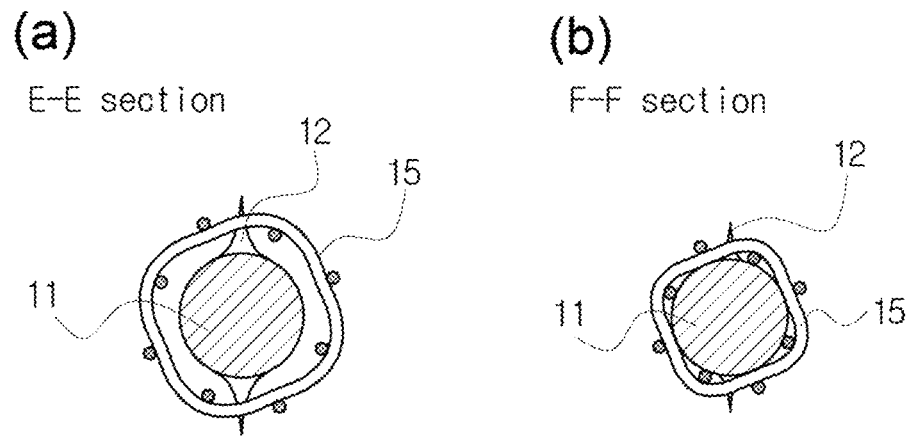
FIG. 5 is a cross-sectional view of the first and second regions of the surgical thread according to one embodiment of the present disclosure.

As illustrated in FIGS. 3 to 5, in a mesh thread 15, a first region i and a second region ii with different mesh shapes are repeatedly formed in a longitudinal direction of the cog thread.

FIG. 3 is a view illustrating the surgical thread according to one embodiment of the present disclosure, FIG. 4 is an enlarged view of portion D of FIG. 3, and FIG. 5 is a view illustrating cross-section (a) of the first region and cross-section (b) of the second region.

Figure 6:
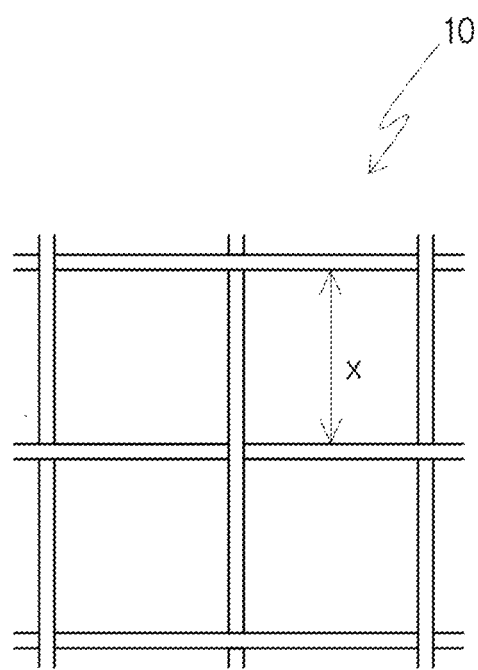
FIG. 6 is a view for describing the definition of an opening of a mesh thread.

In the technical field of mesh, each gap x formed between threads constituting a mesh as illustrated in FIG. 6 is defined as an opening.

The first region i has a diameter that allows cogs 12 of a cog thread 11 to protrude to the outside, and the second region ii has a diameter smaller than the diameter of the first region i. The mesh thread 15 of the second region ii may be in full contact with the cog thread 11. The full contact means that an inner side surface of the mesh thread 15 comes in contact with a portion of the cog thread 11 where the cogs 12 are not formed and presses the cogs 12 at a portion where the cogs are present, and the pressed cogs 12 only partially protrude to the outside of the mesh thread 15. Some of the cogs may not protrude to the outside of the mesh thread. The cogs 12 of the cog thread 11 may be pressed toward the center of the cog thread 11 by the mesh thread 15. In this respect, the cogs 12 of the cog thread 11 are different from the cogs 12 of the first region that protrude, without deformation, to the outside of the mesh thread according to the size of the cogs 12 and the diameter and opening of the mesh thread 15.

Since diameters of individual threads constituting the mesh thread 15 are the same, when an inner diameter of the mesh thread 15 decreases, the opening also decreases. When the inner diameter of the mesh thread 15 decreases, an amount of friction per unit area increases between the individual threads constituting the mesh thread, and accordingly, loosening of the mesh thread is further prevented.

Also, the mesh thread 15 of the second region ii that is in contact with the cogs 12 is less prone to loosening due to elasticity of the cogs 12 and being caught on the cogs 12.

Also, the cog thread 11 at a position corresponding to the second region ii may have a plurality of cogs formed thereon toward different ends of the surgical thread. Such a configuration more reliably prevents the surgical thread from being pushed.

Since the first region i of the mesh thread 15 is a predetermined distance apart from the cog thread 11 as illustrated in FIGS. 4 and 5, living tissue may sufficiently grow inside the mesh thread 15, and even when the mesh thread 15 is pressed toward the cog thread 15 when the surgical thread is inserted subcutaneously, the cogs 12 are sufficiently exposed to the outside of the mesh thread through the openings of the mesh thread 15, and thus the surgical thread may be reliably fixed to subcutaneous tissue.

The first region i of the mesh thread 15 may be formed to be longer than the second region ii, and each second region ii may be formed to have a length in a range of 3 mm to 10 mm.

A transition section where the mesh shape changes is present in the first region i and the second region ii, but of course, the first and second regions may be distinguished based on standards that take the transition section into consideration.

Also, forming both ends of the surgical thread as the second region ii is advantageous in reducing loosening of both ends, and since a diameter difference between the cog thread 11 and the mesh thread 15 is smaller in the second region ii than in the first region I, there are advantageous effects in that, not only is the amount of mesh thread degenerated during heat fusion reduced, but also, even when an adhesive is used, the amount of used adhesive can be reduced.

With the above-described configuration of the present disclosure, a surgical thread of the present disclosure can prevent a mesh thread from being pushed toward an end of the surgical thread, can be easily produced, and can eliminate or minimize heat fusion or the application of an adhesive.

The present disclosure has been described above with reference to the embodiments illustrated in the drawings, but the description is merely illustrative, and those of ordinary skill in the art should understand therefrom that various modifications and other equivalent embodiments are possible. Therefore, the true technical protection scope of the present disclosure should be defined by the claims below.

What is claimed is:

1. A surgical thread comprising:
   a cog thread; and
   a mesh thread surrounding the cog thread and assembled therewith,
   wherein, in the mesh thread, first and second regions with different mesh shapes are repeatedly disposed in a longitudinal direction of the cog thread.

2. The surgical thread of claim 1, wherein a size of an opening of the first region is larger than a size of an opening of the second region.

3. The surgical thread of claim 1, wherein a diameter of the first region is larger than a diameter of the second region.

4. The surgical thread of claim 3, wherein an inner side surface of the mesh thread of the second region is in full contact with the cog thread.

5. The surgical thread of claim 1, wherein the cog thread at a position corresponding to the second region has a plurality of cogs formed thereon toward different ends of the surgical thread.

6. The surgical thread of claim 1, wherein a length of the first region is longer than a length of the second region.

7. The surgical thread of claim 6, wherein the length of the second region is in a range of 3 mm to 10 mm.

8. The surgical thread of claim 1, wherein the length of the second region is in a range of 3 mm to 10 mm.

9. The surgical thread of claim 1, wherein both ends of the surgical thread are formed as the second region.

10. The surgical thread of claim 9, wherein the cog thread and the mesh thread are adhered by an adhesive or heat fusion at the both ends of the surgical thread.

11. The surgical thread of claim 1, wherein the cog thread and the mesh thread are adhered by an adhesive or heat fusion at the both ends of the surgical thread.

* * * * *